United States Patent [19]

Fuisz et al.

[11] Patent Number: 5,456,932
[45] Date of Patent: Oct. 10, 1995

US005456932A

[54] METHOD OF CONVERTING A FEEDSTOCK TO A SHEARFORM PRODUCT AND PRODUCT THEREOF

[75] Inventors: Richard C. Fuisz, Great Falls, Va.; Subraman R. Cherukuri, Towaco, N.J.

[73] Assignee: Fuisz Technologies Ltd., Chantilly, Va.

[21] Appl. No.: 232,835

[22] Filed: Apr. 22, 1994

Related U.S. Application Data

[63] Continuation-in-part of Ser. No. 851,650, Mar. 16, 1992, Pat. No. 5,236,734, which is a continuation-in-part of Ser. No. 602,485, Oct. 24, 1990, Pat. No. 5,096,492, which is a continuation-in-part of Ser. No. 169,838, Mar. 18, 1988, Pat. No. 4,855,326, which is a continuation of Ser. No. 40,371, Apr. 20, 1987, abandoned.

[51] Int. Cl.$^6$ .............................. A23G 3/00; A23G 9/00; A23L 1/236

[52] U.S. Cl. .................. 426/548; 426/519; 426/555; 426/567; 426/588; 426/590; 426/650; 426/658; 426/660

[58] Field of Search .................................. 426/548, 555, 426/567, 588, 590, 650, 658, 660, 519

[56] References Cited

U.S. PATENT DOCUMENTS

| | | |
|---|---|---|
| Re. 32,016 | 10/1985 | Esders et al. . |
| 2,826,169 | 3/1958 | LeVeen . |
| 2,918,404 | 12/1959 | Mende . |
| 3,019,745 | 2/1962 | Du Bois et al. . |
| 3,036,532 | 5/1962 | Bowe . |
| 3,067,743 | 12/1962 | Merton et al. . |
| 3,070,045 | 12/1962 | Bowe . |
| 3,073,262 | 1/1963 | Bowe . |
| 3,095,258 | 6/1963 | Scott . |
| 3,118,396 | 1/1964 | Brown et al. . |
| 3,131,428 | 5/1964 | Mika . |
| 3,308,221 | 3/1967 | Opfell . |
| 3,324,061 | 6/1967 | Tanquary et al. . |
| 3,482,998 | 12/1969 | Carroll et al. . |
| 3,523,889 | 8/1970 | Eis . |
| 3,557,717 | 1/1971 | Chivers . |
| 3,595,675 | 7/1971 | Ash et al. . |
| 3,615,671 | 10/1971 | Schoaf . |
| 3,625,214 | 12/1971 | Higuchi . |
| 3,676,148 | 7/1972 | De Weese et al. . |
| 3,686,000 | 8/1972 | Lawrence . |
| 3,723,134 | 3/1973 | Chivers . |
| 3,749,671 | 7/1973 | Gedge III, et al. . |
| 3,762,846 | 10/1973 | Chivers . |
| 3,766,165 | 10/1973 | Rennhard . |
| 3,856,443 | 12/1974 | Salvi . |
| 3,875,300 | 4/1975 | Homm et al. . |
| 3,876,794 | 4/1975 | Rennhard . |
| 3,907,644 | 9/1975 | Mollering et al. . |
| 3,912,588 | 10/1975 | Mollering et al. . |
| 3,925,164 | 12/1975 | Beaucamp et al. . |
| 3,925,525 | 12/1975 | La Nieve . |
| 3,930,043 | 12/1975 | Warning et al. . |
| 3,951,821 | 4/1976 | Davidson . |
| 3,967,623 | 7/1976 | Butterworth et al. . |
| 3,972,725 | 8/1976 | Nicol . |
| 3,981,739 | 9/1976 | Dmitrovsky et al. . |
| 3,992,265 | 11/1976 | Hansen . |
| 4,056,364 | 11/1977 | Dmitrovsky et al. . |
| 4,072,658 | 2/1978 | Okamoto et al. . |
| 4,086,418 | 4/1978 | Turbak et al. . |

(List continued on next page.)

FOREIGN PATENT DOCUMENTS

| | | |
|---|---|---|
| 609135 | 4/1988 | Australia . |
| 609137 | 4/1988 | Australia . |
| 900605 | 11/1977 | Belgium . |
| 1303511 | 4/1988 | Canada . |
| 0287488A1 | 3/1988 | European Pat. Off. . |
| 0387950A1 | 8/1990 | European Pat. Off. . |
| 0540460A1 | 5/1993 | European Pat. Off. . |
| 86053 | 4/1988 | Israel . |
| 86052 | 4/1988 | Israel . |
| 88/2771 | 4/1988 | South Africa . |
| 88/2770 | 4/1988 | South Africa . |
| 89/9318 | 12/1989 | South Africa . |
| 90/2139 | 3/1990 | South Africa . |
| 90/8406 | 8/1991 | South Africa . |
| 519858 | 4/1971 | Switzerland . |
| 489211 | 7/1986 | Switzerland . |
| 2155934 | 3/1985 | United Kingdom . |
| WO91/07952 | 10/1990 | WIPO . |
| WO91/18613 | 5/1991 | WIPO . |

OTHER PUBLICATIONS

R. H. Doremus, "Crystallization of Sucrose From Aqueous Solution," *Journal of Colloid and Interface Science*, 104, pp. 114–120 (1985).

P. Bennema, "Surface Diffusion and the Growth of Sucrose Crystals," *Journal of Crystal Growth*, 3,4 pp. 331–334 (1968).

T. D. Simpson, et al., "Crystalline Forms of Lactose Produced in Acidic Alcoholic Media," *Journal of food Science*, 47, pp. 1948–1954 (1982).

A. D. Randolph, et al., "Continuous Sucrose Nucleation," *The International Sugar Journal*, pp. 8–12 (1974).

K. B. Domovs, et al., "Methanol–Soluble Complexes of Lactose and of other Carbohydrates," *J. Dairy Science*, 43, pp. 1216–1223 (1960).

A. D. Randolph, et al., "Continuous Sucrose Nucleation," *The International Sugar Journal*, pp. 35–38 (1974).

A. D. Randolph, et al., "Continuous Sucrose Nucleation," *The International Sugar Journal* pp. 73–77 (1974).

ICI Americas Inc., "ICI Americas Products for Cosmetics and Pharmaceuticals," (1977).

Domino Sugar Corporation, "Co–crystallization".
Domino Sugar Corporation, "Raspberry".
Domino Sugar Corporation, "Molasses Dark".

*Primary Examiner*—Arthur L. Corbin
*Attorney, Agent, or Firm*—Hoffmann & Baron

[57] ABSTRACT

The present invention is a new process for flash flow processing a feedstock containing a heat sensitive ingredient and a carrier material selected from a maltodextrin and polydextrose and the product resulting therefrom. The process and product includes the use of fructose as a processing aid in an amount sufficient to reduce the amount of heat required to create flashflow conditions in the carrier portion of the feedstock.

25 Claims, No Drawings

U.S. PATENT DOCUMENTS

| | | |
|---|---|---|
| 4,090,920 | 5/1978 | Studer, Jr. . |
| 4,136,145 | 1/1979 | Fuchs et al. . |
| 4,153,512 | 5/1979 | Messner et al. . |
| 4,159,210 | 6/1979 | Chen et al. . |
| 4,160,696 | 7/1979 | Wu . |
| 4,164,448 | 8/1979 | Rosechlau et al. . |
| 4,168,205 | 9/1979 | Danninger et al. . |
| 4,186,251 | 1/1980 | Tarbutton . |
| 4,194,063 | 3/1980 | Frank et al. . |
| 4,199,373 | 4/1980 | Dwivedi et al. . |
| 4,241,178 | 12/1980 | Esders et al. . |
| 4,293,570 | 10/1981 | Vadasz . |
| 4,303,684 | 12/1981 | Pitchon et al. . |
| 4,335,232 | 6/1982 | Irwin . |
| 4,338,350 | 7/1982 | Chen et al. . |
| 4,348,420 | 9/1982 | Lynch et al. . |
| 4,362,757 | 12/1982 | Chen et al. . |
| 4,371,516 | 2/1983 | Gregory et al. . |
| 4,376,743 | 3/1983 | Dees . |
| 4,382,963 | 5/1983 | Klose et al. . |
| 4,382,967 | 5/1983 | Koshida et al. . |
| 4,492,685 | 1/1985 | Keith et al. . |
| 4,496,592 | 1/1985 | Kuwahara et al. . |
| 4,500,546 | 2/1985 | Turbak et al. . |
| 4,504,509 | 3/1985 | Bell et al. . |
| 4,511,584 | 4/1985 | Percel et al. . |
| 4,526,525 | 7/1985 | Oiso et al. . |
| 4,585,797 | 4/1986 | Cioca . |
| 4,619,833 | 10/1986 | Anderson . |
| 4,765,991 | 8/1988 | Cherukuri et al. . |
| 4,772,477 | 9/1988 | Weiss et al. . |
| 4,793,782 | 12/1988 | Sullivan . |
| 4,816,283 | 3/1989 | Wade et al. . |
| 4,853,243 | 8/1989 | Kahn et al. . |
| 4,855,326 | 8/1989 | Fuisz . |
| 4,871,501 | 10/1989 | Sugimoto . |
| 4,872,821 | 10/1989 | Weiss . |
| 4,879,108 | 11/1989 | Yang et al. . |
| 4,885,281 | 12/1989 | Hanstein et al. . |
| 4,978,537 | 12/1990 | Song . |
| 4,988,529 | 1/1991 | Nakaya et al. . |
| 4,997,856 | 3/1991 | Fuisz . |
| 5,011,532 | 4/1991 | Fuisz . |
| 5,028,632 | 7/1991 | Fuisz . |
| 5,037,662 | 8/1991 | Poulose et al. . |
| 5,039,446 | 8/1991 | Estell . |
| 5,041,377 | 8/1991 | Becker et al. . |
| 5,066,218 | 11/1991 | Silver . |
| 5,073,387 | 12/1991 | Whistler . |
| 5,077,076 | 12/1991 | Gonsalves et al. . |
| 5,082,682 | 1/1992 | Peterson . |
| 5,082,684 | 1/1992 | Fung . |
| 5,084,295 | 1/1992 | Whelan et al. . |
| 5,089,606 | 2/1992 | Cole et al. . |
| 5,094,872 | 3/1992 | Furcsik et al. . |
| 5,096,492 | 3/1992 | Fuisz . |
| 5,104,674 | 4/1992 | Chen et al. . |
| 5,110,614 | 5/1992 | Corbin et al. . |
| 5,173,322 | 12/1992 | Melachouris et al. . |
| 5,196,199 | 3/1993 | Fuisz . |
| 5,238,696 | 8/1993 | Fuisz . |
| 5,279,849 | 1/1994 | Fuisz . |
| 5,286,513 | 2/1994 | Fuisz . |
| 5,288,508 | 2/1994 | Fuisz . |
| 5,387,431 | 2/1995 | Fuisz ........................ 426/658 |

5,456,932

METHOD OF CONVERTING A FEEDSTOCK TO A SHEARFORM PRODUCT AND PRODUCT THEREOF

This application is a continuation-in-part of PCT patent application Ser. No. PCT/US93/04362 filed May 4, 1993, which is a continuation-in-part of U.S. Ser. No. 7/851,650, filed Mar. 16, 1992, now U.S. Pat. No. 5,236,734, which is a continuation-in-part of U.S. Ser. No. 602,485 filed Oct. 24, 1990, now U.S. Pat. No. 5,096,492, which in turn is a continuation-in-part of U.S. Ser. No. 169,838, filed Mar. 18, 1988, now U.S. Pat. No. 4,855,326, which in turn is a continuation of U.S. Ser. No. 040,371, filed Apr. 20, 1987, now abandoned.

BACKGROUND OF THE INVENTION

The present invention relates to flash flow processing, and, in particular, to a method of improving flash flow processing. The present invention also relates to improving the product of flash flow processing.

Flash flow processing is referred to as the process in which a phenomena occurs wherein a solid carrier material is subjected to conditions of temperature and shear sufficient to provide internal flow at a subparticle level. This condition produces the transformation of physical and/or chemical structure. Internal flow occurs when the infrastructure of the material breaks down sufficiently to permit movement of a particle at a subparticle level, and probably at a molecular level. At a molecular level, internal flow contemplates the movement of molecules relative to each other.

Flash flow phenomena occurs in a very short time, usually not more than a second, preferably on the order of a tenth of a second. One method of producing flash flow processing conditions includes subjecting a feedstock material to flash heat in the presence of centrifugal force provided by a spinning head, such as in a cotton candy type machine. The heat, which is provided by a heating element along the wall of the spinning head, is considered to provide flash heat, which, when combined with the centrifugal force provided by the spinning head, induces deformation of the feedstock material through openings located in the wall of the spinning head. The material reforms as a solid having altered, physical and/or chemical structure.

In U.S. Pat. No. 4,855,326, issued Aug. 8, 1989 to Dr. Richard C. Fuisz, various substances having pharmacological properties are disclosed as being combined with sugar and spun into fibers to produce a readily watersoluble product. Another patent issued to Dr. Fuisz regarding flash flow processing is U.S. Pat. No. 5,011,532 issued Apr. 30, 1991, which discloses combining oleaginous substances with sugar and melt spinning the mixture in a cotton candy spinning machine or the equivalent. Other disclosures which relate to spinning substances with one or more sugars are found in U.S. Pat. No. 4,873,085 issued Oct. 8, 1989, U.S. Pat. No. 5,034,421 issued Jul. 23, 1991, U.S. Pat. No. 5,028,632 issued Jul. 2, 1991, and U.S. Pat. No. 4,997,856 issued Mar. 5, 1991. The products described in the abovementioned patents are all produced by processing in a cotton candy type machine.

There is no indication in any of the references cited above, however, of the use of certain ingredients to modify the composition of the feedstock and thereby improve the process and product resulting therefrom.

It is, therefore, an object of the present invention to provide such a method and the product resulting therefrom.

SUMMARY OF THE INVENTION

The present invention is an improvement in a method for converting feedstock which contains a carrier component selected from either a maltodextrin and/or polydextrose. The conversion is one in which the feedstock is converted to a shearform product. The improvement includes the addition of fructose to the feedstock in an amount sufficient to reduce the amount of heat which must be added in order to obtain flash flow conditions in the carrier portion of the feedstock. Preferably, the improvement reduces the amount of heat required to a temperature of between 10°–25° C. below the flash flow temperature of the feedstock without the addition of fructose.

Further ingredients which can be added to the feedstock include, but are not limited to, medicaments, frozen food ingredients, confectionery ingredients, dry beverage ingredients, cake mix ingredients, and flavorants.

The present invention also includes a comestible shearform product prepared as set forth above. The amount of fructose added is sufficient to enhance the flavor of the resulting product.

In terms of composition, the amount of fructose included in the feedstock can be in a range of from about 5% to about 50% by weight of the feedstock, and is preferably at a range of from about 10% to about 40% of the overall weight of the feedstock. The feedstock can be a composition in which non-fructose carrier material is at least about 30% of maltodextrin, polydextrose, and mixtures thereof.

The flavorants include sweeteners which can be either natural or artificial sweeteners. When the sweeteners are artificial sweeteners, they can include ingredients selected from the group consisting of saccharine, saccharine salts, cyclamic acid, cyclamic acid salts, aspertame, sucralose, acesulfame and combinations thereof.

When the sweeteners are natural sweeteners, they can be selected from the group consisting of sucrose, maltose, dextrose, ribose, lactose, glucose, arabinose, mannose, pentose, sorbose, xylose, galactose, sorbitol, mannitol, galactitol, lactitol, maltitol, and mixtures thereof.

When the ingredient is a food acid, they can be selected from the group consisting of malic acid, citric acid, tartaric acid, adipic acid, fumaric acid, ascorbic acid and mixtures thereof.

When frozen food ingredients are included, they can include hydrogels, emulsifiers, nutritional supplements, dehydrated vegetable fluids, nonfat milk solids, dehydrated animal fluids, vitamins and minerals.

The present invention also includes a confectionery tabletting ingredient which can be directly compressed without further processing by transformation of a shearform comestible as set forth above. Moreover, the present invention includes dry beverage mix and cake mix processed as set forth above.

In a most preferred embodiment, the present invention includes a method for preparing an enzyme containing material, especially a heat-sensitive enzyme. An excellent example of this embodiment is the preparation of non-fat dry milk solids. Non-fat dry mild solids can be flash flow processed with maltodextrins or polydextrose or a mixture thereof in the presence of fructose at a significantly reduced temperature so that the heat-sensitive enzyme component is preserved in the resulting matrix material. As a result of this process, a non-fat ice cream ingredient can be successfully prepared for sale, shipment, and use at a later date.

As a result of the present invention, shearform matrixes prepared by flash flow processing are considerably improved. This is achieved by reducing a temperature at which the feedstock (the carrier and non-carrier material) will undergo flash flow to permit transformation from a solid to a solid. The resulting matrix has reduced flossiness and hardness and has a better uniform mixture.

Moreover, the effective heat on the components, especially volatile components, is significantly reduced thereby increasing the ability of processing such components by flash flow. Moreover, components which could not be considered for flash flow processing can now be used and higher loading can be achieved by incorporating fructose in the feedstock material.

Another benefit of the present invention is that an enhanced flavor results from inclusion of fructose in the feedstock material. A rounder sweetness which results from natural fruit characteristics of fructose is expressed in the resulting matrix product.

Moreover, the combination of fructose with other sweeteners generally results in a synergism which is unexpected. For example, when the fructose is combined with, for example, corn syrup solids, the combination should result in 120% sweetness of the corn syrup solids. However, the combination resulting from the present invention has a sweetness which is 150% of the natural sweetness of corn syrup solids.

The reduced temperature processing is also quite dramatic. For example, when maltodextrins are used, the melting point is around 140°–150° C., when combined with fructose in accordance with the present invention, the flash flow temperature can be reduced to around 100°–120° C. In the case of polydextrose, the flash flow processing temperature is around 160°–170° C., but when combined with fructose in accordance with the present invention, the resulting flash flow temperature can be reduced to about 110°–135° C.

DETAILED DESCRIPTION OF THE INVENTION

The present invention is an improved method for converting a feedstock which contains a saccharide-based carrier material to a shearform product. The "carrier portion" of a feedstock is that portion which undergoes a transition in structure. Upon subjecting a carrier containing feedstock to flash-flow conditions, the carrier portion has physically and/or chemically altered structure when compared to the pretreated carrier. In the present invention, maltodextrins and polydextrose are used as carrier materials.

Saccharide-based products can have varying degrees of low-monomer saccharides (or sugars), oligomers, and polysaccharides, such as starch. Some saccharide-based products are prepared by hydrolysis of starch and are classified by the degree of starch polymer hydrolysis. The measuring unit is referred to as D.E. or dextrose equivalent. D.E. is defined as reducing sugar that is expressed as dextrose and reported as a percentage of the dry substance.

A saccharide-based product having a high short carbon chain content, e.g., glucose and low-unit oligomers thereof, usually result in a higher dextrose equivalent. However, saccharide-based material having greater long-carbon-chain content, e.g., high-monomer unit oligomers and polymers, usually results in a lower D.E. rating.

The feedstock of the present invention can include a saccharide-based product which is referred to herein as a maltodextrin.

Maltodextrins contain a mix of sugars and polysaccharides which range from long-chain oligomers resulting from starch hydrolysis to sugars having a low number of monomeric units. Under FDA guidelines maltodextrin consists of nonsweet, nutritive saccharide polymers having a D.E. of less than 20, while corn syrup solids is regarded by the FDA as having a D.E. greater than 20. The present inventor, however, refers to maltodextrins collectively as solid saccharide-based material consisting of nonsweet, nutritive saccharide polymers and other oligomers having six-carbon monomer units which collectively provide a carrier material capable of forming a matrix including maltodextrins having a D.E. of up to 45.

Maltodextrins have been used as a nonfat additive. One of the greatest advantages of maltodextrins is that they do not act adversely on the intestinal tract. Consequently, they are particularly useful as a bulking agent and as a fat substitute. Moreover, maltodextrins are generally recognized as safe (GRAS) by the United States Food and Drug Administration.

Unfortunately, the ability to disperse maltodextrins and use them in different products is limited by their physical and chemical cohesiveness. They are unlike their high sugar counterparts in that they are relatively unreactive and physically resistive to mixing and dispersing. While artisans have been able to process sugar to enhance its utility in food and medicaments, the maltodextrins do not appear to be as versatile. In a series of commonly owned applications, Dr. Fuisz has disclosed his discovery of how to process maltodextrins by flash flow processing. See U.S. application Ser. No. 099,200 filed Jul. 29, 1993, which is a continuation-in-part of U.S. application Ser. No. 07/847,595 filed on Mar. 5, 1992, now U.S. Pat. No. 5,387,431, which in turn is a continuation-in-part of U.S. application Ser. No. 07/782,430, filed on Oct. 25, 1991, now abandoned.

The maltodextrins useful as carriers in the present invention are those mixtures resulting from hydrolysis as described above which have a D.E. of up to 45. The higher D.E. solid maltodextrins are within the scope of the present invention. Maltodextrins which are useful in the present invention include some products which are sold under the trademark MALTRIN®, a product of the Grain Processing Corporation of Muscatine, Iowa.

In a preferred embodiment of the present invention the carrier used in the feedstock of the present invention is a deionized form of maltodextrin. Deionization, in general, refers to the procedure whereby ionic impurities are removed by, for example, passing the material to be deionized through cation and/or anion exchange columns. In a present preferred embodiment deionized maltodextrin ENZOSE 42DE, a product of CPC International, has been found to be particularly beneficial as a carrier for the feedstock of the present invention.

Another carrier material contemplated for use in the present invention is polydextrose.

Polydextrose is a non-sucrose, essentially non-nutritive carbohydrate substitute. Polydextrose can be prepared through polymerization of glucose in the presence of polycarboxylic acid catalysts and polyols. Generally, polydextrose is known to be commercially available in three forms: polydextrose A and polydextrose K, which are powdered solids, and polydextrose N supplied as a 70% solution. Each of these products also contain some low molecular weight components, such as glucose, sorbitol and certain oligomers.

Most of the interest in polydextrose has centered around its use in various edible compositions. For example, polydextrose has stimulated interest in the food arts as a low-calorie bulking agent or as a part of many low-calorie or light foods since it has only about one-quarter of the calories of sucrose. Non-food related uses for the material have largely been ignored.

The solid forms of polydextrose are in a form which is somewhat like powdered milk. As such, it can be difficult to disperse or dissolve. Vigorous stirring is required to incorporate it into water or aqueous liquids and it can lump or form difficult-to-disperse clumps of material, i.e., the "fisheye" phenomenon. In contrast thereto, the melt-spun polydextrose-containing products of the present invention enter into a dispersion in aqueous liquids with little or no mechanical agitation. Thus, the melt-spun polydextrose of the invention overcomes certain processing difficulties such as clumping and inability to flow in a dry state. Further, the novel polydextrose-containing compositions of this invention, in addition to enhanced dispersion properties, can be used to hold one or more ingredients combined in the matrix and release it over time. In commonly-owned, application and issued patent, Dr. Fuisz has disclosed a method of processing polydextrose by flash flow in order to enhance the dispersability of polydextrose. See U.S. application Ser. No. 019,097 filed Feb. 18, 1993, which is a continuation-in-part of U.S. application Ser. No. 881,612 filed Apr. 29, 1991, now abandoned, and U.S. Pat. No. 5,279,849 issued Jan. 18, 1994, which matured from U.S. application Ser. No. 881,603 filed on May 12, 1992.

As previously noted, the improved method of the present invention is that of a flash flow processing. The shearform process is one in which a feedstock is subjected to shear and heat simultaneously in order to obtain flash flow. One shearform process includes subjecting a feedstock to shear created by high speed spinning on a spinning head. The spinning head casts the material outwardly as the feedstock undergoes flash flow. Flash flow is created as a consequence of simultaneous application of heat and shear.

An alternative shearform process includes heating a non-solubilized feedstock having a carrier sufficiently to provide internal flow. The feedstock is ejected while the carrier possesses internal flow, and is then subjected to disruptive fluid shear force to form multiple masses of carrier. Other methods are contemplated which provide the same critical conditions of heat and shear wherein a substantially solid feedstock containing a maltodextrin or polydextrose can be transformed physically and/or chemically from a solid structure to an essentially amorphous solid structure.

One of the preferred methods for melt-spinning is through the use of apparatus such as those adapted to the production of cotton candy, or floss, from sugar. Illustrative of such machines is the Econo Floss Machine Model 3017 manufactured by Gold Medal Products Company of Cincinnati, Ohio. It will be appreciated by those skilled in the art from the present description that any apparatus or physical process which provides similar shear forces and time/temperature gradient conditions can also be used. For simplicity in disclosing and describing this invention, the term "melt-spinning" will be understood to mean a flash flow process which includes a combination of temperature, shear, flow, flow rate, mechanical forces and thermal gradients of the type used in a cotton candy-type machine.

More recently, commonly owned application entitled "Process For Making Shearform Matrix," filed on Oct. 23, 1992 and assigned U.S. application Ser. No. 965,804, now U.S. Pat. No. 5,380,473 discloses another process for making shearform matrix by subjecting non-solubilized feedstock to heat sufficient to induce internal flow, ejecting a stream of the feedstock while possessing internal flow, and then subjecting it to disruptive fluid shear force which separates it into separate parts or masses having transformed morphology. The product is amorphous.

In both of the cases set forth above, the carrier material must be raised to the temperature of flash flow before it can undergo transformation. As a result of the present invention, it has been discovered that the flash flow temperature can be significantly reduced. The benefits of reducing the flash flow condition in the carrier material are many. First of all, the number of ingredients which can now be included in the feedstock which were otherwise not available because of the possibility of deterioration or volatilization are significantly increased. Moreover, higher loading of added materials results because of the once again low temperature in which the carrier can be processed. A somewhat unexpected result is that the taste of products which include sweeteners is significantly enhanced.

This improved process has been achieved simply by the addition of fructose as a processing aid. Over the years, fructose has been used primarily as a sweetener. The sweetness of fructose is 1.3–2.0 times that of sucrose, which makes it an attractive alternative to sucrose. For example, U.S. Pat. No. 4,271,199 discloses the use of fructose in a chewing gum having soft and smooth consistency, in which the fructose is used in a recrystallized form made from high fructose syrup liquid in combination with solid sucrose or sorbitol in water.

Fructose is also known as a flavor enhancer. When used as a bulk sweetening agent in a chewing gum composition, fructose provides a clean, pleasant taste to the chewing gum composition which has an improved rate of flavor and sweetness perception. A synergistic sweetness effect exists between sucrose and fructose. A 40%–60% fructose/sucrose mixture in 100% water solution is sweeter than either component under comparable conditions. However, the use of crystalline fructose as a bulk sweetening agent for chewing gums or other applications has been disfavored because in its crystalline form fructose imparts a gritty mouthfeel. For example, in U.S. Pat. No. 4,271,199 to Cherukuri et al. crystalline fructose was used in combination with other sweetening agents to avoid imparting the chewing gum mixture the gritty mouthfeel. Similarly, U.S. Pat. No. 4,900,563 also to Cherukuri et al. discloses fructose-sweetened chewing gum compositions having an enhanced flavor and sweetness obtained through the use of powdered fructose as a bulk sweetening agent.

Fructose is commercially available in dry crystalline form or as high fructose corn syrup containing from 40 to about 90% fructose. In its commercially available forms fructose has poor compression properties and cannot be used as tabletting material without extensive prior treatment steps. Therefore, it is very surprising, indeed, that feedstock flash flow processed with fructose as a processing aid can provide an enhanced tabletting matrix.

Fructose is known as the commonest of ketoses and the sweetest of sugars. It is also known as D-fructose, D-fructopyranose, levulose or fruit sugar $C_6H_{12}O_6$. It is found in free state, usually accompanied by D-glucose and sucrose in fruit juices, honey, and nectar of plant glands. D-fructose can be isolated as crystalline β-D-fructopyranose which has a melting point between 102°C.–104° C. (217°F.–219°F.). Commercially processed fructose is available as white crystals, soluble in water, alcohol and ether.

Fructose can be derived by the hydrolysis of inulin, beet sugar followed by lime separation, and from corn starch by enzymic or microbial action. D-fructose is more soluble in water than D-glucose and has a much sweeter taste.

High-fructose corn syrup is produced by affixing enzymes to solid carriers and passing corn syrup over them to transform glucose into fructose. High-fructose corn (maze) syrup contains over 90% fructose and has a sweetening power of between 120 and 160 (sucrose=100). Thus, calorie reduction is possible because of an increase in perceived sweetness.

Other uses of fructose are disclosed in commonly-assigned U.S. Pat. Nos. 4,855,326; 4,873,085; 5,028,632; 5,034,421; 5,196,199 issued to Dr. Fuisz. In these disclosures fructose is used by itself or with other simple sugars as carrier in a feedstock containing active agents having pharmacological and/or cosmetic properties to produce readily water-soluble or water dispersable shearform products. In the foregoing Fuisz patents, the carrier materials are processed in a conventional cotton candy spinning machine. None of these patents disclose the use of fructose as a processing aid or a flavor enhancer.

U.S. Pat. No. 5,238,696 issued to Dr. Fuisz discloses fructose used as a carrier for oleaginous materials. In the '696 patent fructose is subjected to flash-flow conditions to form an oleaginous-containing matrix which can be mixed with frozen food ingredients such as ice cream, frozen custard, ice milk, sherbet, frozen dairy desserts, whipped toppings, frostings and puddings to form new frozen comestibles. Maltodextrins or polydextrose can be used as alternative carrier materials.

In U.S. Pat. No. 5,236,734 also issued to Dr. Fuisz, fructose and polydextrose are used as carrier materials for oleaginous substances to form melt-spun matrixes which can be mixed with proteinaceous materials to provide hamburgers or soyburgers. Maltodextrins and water soluble cellulosic materials are used as alternative carriers.

In both the '696 and '734 patents, the flash-flow process contemplates subjecting carrier solids to a melt-spun process or comparable conditions to provide sufficient internal flow in the carrier material in order to permit movement of the material at subparticle level. The internal flow of carrier material is generally associated with the melting point or glass transition point of the carrier material. For example, in the '696 patent, the feedstock material was subjected to flash-flow conditions at operating temperatures of approximately 200° C. which is close to the melting point of sucrose. The spun products disclosed in these patents are described as taking the form of a floss or a mass of spun fibers. None of the above disclosures describe the use of fructose as an additive for lowering the amount of added heat required to create flash flow conditions in the carrier portion of the feedstock. None of these disclosures suggest using fructose as an additional flavor enhancer for the food products containing it.

Other disclosures discussing fructose and its uses are found in commonly assigned International and U.S. applications PCT/US92/10978; PCT/US92/04048; 07/964,022, now U.S. Pat. No. 5,438,758 08/071,176 by Dr. Fuisz. In these disclosures fructose is used by itself or in combination with polydextrose or maltodextrin in a feedstock. The feedstock contains actives such as anti-ulcer medicaments, enzymes, or comestible ingredients such as oleaginous materials or starch. Upon subjecting the feedstock to flash flow conditions a variety of desirable modified products are provided such as more rapidly soluble anti-ulcer compositions, more easily dispersable or dissoluble enzymes, an amorphous antihumectant bearing matrix used to form a controlled melting point product, or enhanced starch products used as fat replacement in protein based products. None of these disclosures describe or use fructose from about 5% to about 50% as a processing aid or a provider of additional flavor enhancement.

Fructose is also described as a carrier in International application Number PCT/US92/09447 also by Dr. Fuisz. In this disclosure, fructose, maltodextrins and polydextrose are used as carriers to form a flash-flowable matrix which acts as an encapsulant or delivery system for micronized liquid droplets of flavor or aromatic oils. The delivery systems disclosed in this application are used to provide enhanced flavor and/or sweetness due to the flavor oil being finely dispersed in the sweetener matrix (P16, L24). Nevertheless, this application does not disclose the fructose as a processing aid or a sweetener. More importantly, fructose is not used to enhance the durability of flavors with which it comes into contact.

U.S. Pat. No. 5,288,508 describes the use of fructose as both a carrier and a sweetener. Fructose, polydextrose and maltodextrins are described as carrier materials for an additional flavorant which is incorporated into a chewing gum composition in order to provide a chewing gum composition where the flavor is released sequentially, first from the elastomer solvent matrix of a gum base and then from the saccharide-based matrix also included in the chewing gum composition. Fructose is also disclosed as a sweetener which could be added to the elastomer solvent carrier of a gum base. This application does not disclose the use of fructose as a processing aid or as flavor enhancer.

Another disclosure describing the use of fructose as both a carrier and a sweetener is U.S. application Ser. No. 07/782,430 also by Dr. Fuisz, now abandoned. Fructose and other simple sugars such as sucrose or lactose are used as carriers in a feedstock containing flavoring agents and sweeteners. Upon subjecting the feedstock to flash-flow conditions the flavoring agents and sweeteners are combined with the carrier material and become rapidly water soluble or dispersable. Upon mixing with a receiving liquid the flavor release is better than that of untreated flavoring agents or sweeteners because as part of a highly soluble melt-spun matrix the flavor or sweetener have enhanced exposure. There is no disclosure to use fructose as a processing aid or a product enhancer providing additional flavor enhancement.

Maltodextrins and polydextrose which undergo flash-flow at lower temperatures than sucrose are also disclosed as carriers in the '430 application, particularly for heat sensitive artificial sweeteners. Nevertheless, even maltodextrins and polydextrose undergo flash-flow conditions at high temperatures from about 140° C. to about 165° C.

Another use of fructose is disclosed in U.S. application Ser. No. 08/019,097. In this disclosure, fructose or maltodextrins in an amount of less then 5% by weight are used as a wetting agent which are added to a flowable polydextrose feedstock prior to undergoing flash-flow conditions. The use of such wetting agents improves the dispersability of large amounts of polydextrose into aqueous media.

Generally, the disclosures discussed above describe methods of using fructose as a sweetener or a carrier where conventional flash-flow conditions occur at elevated temperatures. These methods are energy intensive and not recommended for use with very heat sensitive materials.

It would, therefore, be a significant advancement in the art of forming shearform products to provide methods of making shearform products at temperatures significantly lower than those conventionally required to create flash-flow conditions in the carrier portion of the feedstock. Such methods provide important energy savings and allow flash-flow processing of heat sensitive materials.

The present invention concerns providing a method for reducing the amount of added heat required to create flash-flow conditions in the maltodextrin or polydextrose carrier portion of a feedstock by using fructose. Surprisingly, it has been unexpectedly discovered that when fructose is added to a maltodextrin or polydextrose carrying feedstock, the amount of heat required to create flash-flow conditions in the carrier portion of the feedstock is reduced by 10°C–25° C. below that required for a non-fructose containing feedstock. As a result of the unique combination in the feedstock of maltodextrins or polydextrose as carrier material the amount of added fructose required to reduce the amount of added heat is from at least about 5% to about 50% by weight as a processing aid, and most preferably from about 25% to about 50% by weight of the feedstock. When the indicated amount of fructose is added, maltodextrin undergoes flash flow conditions from about 110° C. to about 115° C. and polydextrose from about 110° C. to about 130° C.

As used in this invention, "added heat" is the amount of heat required to create internal flow of the carrier material. Internal flow of material is generally associated with melting point or glass transition point of the carrier material. For example, in commonly assigned U.S. Pat. Nos. 4,873,085; 4,997,856; 5,028,632 and 5,034,421 sucrose was used as a carrier for other ingredients such as cosmetic or pharmaceutical agents. In these disclosures the sucrose containing feedstock was subjected to flash-flow conditions from about 200°–260° C. to obtain shearform products in the form of floss or fiber. Carrier materials such as maltodextrins and polydextrose which melt at elevated temperatures such as 140°–150° C. for maltodextrins and 160°170° C. for polydextrose require less added heat than sucrose to undergo flash-flow conditions.

The method of the present invention also includes incorporating other ingredients in the feedstock, especially those which are heat sensitive or tend to char or become denatured if exposed to processing at elevated temperatures. Such ingredients include but are not limited to bio-affecting agents, flavorants, food acids, confectionery ingredients, dry beverage ingredients, cake mix ingredients, frozen food ingredients, condiments and the like.

A non-limiting list of bio-affecting agents useful in the methods of the present invention is as follows: antitussives, antihistamines, decongestants, alkaloids, mineral supplements, laxatives, vitamins, antacids, ion exchange resins, anti-cholesterolemics, anti-lipid agents, antiarrhythmics, antipyretics, analegesics, appetite suppressants, expectorants, anti-anxiety agents, anti-ulcer agents, anti-inflammatory substances, coronary dilators, cerebral dilators, peripheral vasodilators, anti-infectives, physcho-tripics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypnotics, anti-emetics, anti-nauseants, anti-convulsants, neuromuscular drugs, hyper and hypoglycemic agents, thyroid and antithyroid preparations, diuretics, antispasmodics, uterine relaxants, mineral and nutritional additives, antiobesity drugs, anabolic drugs, erythropoietic drugs, antiasthmatics, cough suppressants, mucolytics, anti-uricemic drugs and mixtures thereof.

Flavorants may be selected from sweeteners, food acid, and flavoring agents. Sweeteners useful in the method of this invention may be selected from a wide range of materials including water-soluble sweetening agents, water-soluble artificial sweeteners, water-soluble sweetening agents derived from naturally occurring water-soluble sweeteners, dipeptide based sweeteners, and protein based sweeteners, including mixtures thereof.

Representative examples of water-soluble sweetening agents include monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochancones, monellin, steviosides, glycyrrhizin, and sugar alcohols such as sorbitol, xylitol, mannitol, maltitol, hydrogenated starch hydrolysate and mixtures thereof.

Representative examples of water-soluble artificial sweeteners include the soluble saccharin salts, i.e., sodium or calcium saccharin salts, cyclamate salts, the sodium, ammonium or calcium salt of 3,4-dihydro-6-methyl-1,2,3- oxathiazine-4-1-2,2-dioxide, the potassium salt of 3,4-dihydro-6-methyl-1,2,3-oxathiazine-4-1-,2,2-dioxide (acesulfame-K) the free acid form of saccharin, and the like.

Representative examples of dipeptide based sweeteners include L-aspartic acid derived sweeteners, such as L-aspartyl-L-phenylalanine methyl ester (aspartame) and materials described in U.S. Pat. No. 3,492,131, L-α-aspartyl-N-(2,2,4,4-tetramethyl-3-thietanyl)-D-alaninamide hydrate, methyl esters of L-aspartyl-L-phenylglycerine and L-aspartyl-L-2,5,dehydrophenylglycine, L-aspartyl-2,5-dihydro-L-phenylalamine; L-aspartyl-L-(1-cyclohexyen)-alanine; and the like.

Food acid flavorants which are useful in the present invention include those generally used with foods such as malic acid, citric acid, tartaric acid, adipic acid, fumaric acid, ascorbic acid, mixtures thereof and the like.

Flavoring agents may be chosen from natural and synthetic flavoring liquids. An illustrative list of flavoring agents includes volatile oils, synthetic flavor oils, flavoring aromatics, oils, liquids, oleoresins or extracts derived from plants, leaves, flowers, fruits, stems and combination thereof. A non-limiting representative list of examples includes citrus oils such as lemon, orange, lime and grapefruit and fruit essences including apple, pear, peach, grape, strawberry, raspberry, cherry, plum, pineapple, apricot and other fruit flavors.

Other useful flavorings include aldehydes and esters such as benzaldehyde (cherry, almond), citral, i.e., alphacitral (lemon, lime), neral, i.e., beta-citral (lemon, lime), decanal (orange, lime), aldehyde C-8 (citrus fruits), aldehyde C-9 (citrus fruits), aldehyde C-12 (citrus fruits), tolyl aldehyde (cherry, almond), 2,6-demethyloctanal (green fruit), and decanal (citrus, mandarin), mixtures thereof, and the like.

Other classes of food products which can benefit from the reduced amount of heat necessary to create flash-flow conditions in the maltodextrin or polydextrose carrier portion of the feedstock are frozen food ingredients, cake mixes and dry beverage mixes. Frozen food ingredients include but are not limited to hydrogels, emulsifiers, nutritional supplements, dehydrated vegetable fluids, dehydrated animal fluids, non-fat mix solids, vitamins and minerals.

As a result of using fructose as a processing aid high concentrations of non-fat milk solids up to at least 30% of the feedstock can be subjected to flash-flow conditions because the addition of fructose permits applying flash-flow conditions at 110° C.–115° C. which is considerably lower than 140° C.–165° C. which is the temperature where maltodextrins typically undergo flash-flow. For example, U.S. Pat. No. 5,238,696 to Fuisz discloses frozen desserts such as an ice cream formed by combining a comestible composition such as an ice cream ingredient with a matrix formed by subjecting an oleaginous substance and a carrier material such as sucrose or maltodextrins to flash-flow conditions. The operating temperatures at which the melt-spun matrix is formed are approximately 200° C. At such elevated temperatures, common ice cream ingredients such as non-fat milk solids become denatured or charred.

Ingredients used in dry beverage mixes which are useful in the present invention include sugar, citrus, fruit flavors, low calorie ingredients such as polydextrose, palatinit, low calorie celluloses and food gums.

Cake mix ingredients also benefit from lower temperatures at which the carrier of a feedstock undergoes flash flow conditions. Cake mix ingredients useful in the method of the present invention include low fat cake ingredients, and any conventional cake ingredients used for preparation of cake mix.

The resulting shearform products obtained by the method of this invention are in fine granular form. As a result, it has been surprisingly found that the granules are directly compressible into tablets thereby enabling the artisan to omit extensive prior treatment steps associated with conventional tabletting methods such as wet or dry granulation.

Other tabletting ingredients which can be mixed with the granular shearform products of the present invention are small amounts of tabletting lubricants and colorants. Useful tabletting lubricants or glidants include magnesium and calcium stearate, zinc stearate, diboric calcium, phosphate, magnesium carbonate, magnesium oxide, calcium silica and silica aerogels.

Colorants suitable for confectionery tabletting may be selected from any of the numerous food, drug and cosmetic dyes known as FD&C dyes and the like. Even though colorants for use herein are preferably water-soluble, the normally non-water soluble colorants can also be included when spun with the carrier material. A full recitation of all FD&C and D&C dyes and their corresponding chemical structures may be found in the Kirk-Othmer Encyclopedia of Chemical Technology, in Volume 5, pages 857–884, which is incorporated herein by reference.

In another aspect of the present invention the granular shearform products provided by the method of this invention can be easily incorporated into other foodstuffs. It has been surprisingly found that when incorporated into other flavor containing foodstuffs, the resulting product exhibits an additional flavor enhancement. As used in the present invention an additional flavor enhancement refers to increased organoleptic perception in the oral cavity of sweetness perception, heightened taste, mouthfeel, tartness or pungency. For example, when granular shearform products of the present invention were added to trace amounts of cherry or orange flavors the resulting tablets had a very intense, immediate, unusually long-lasting and well balanced cherry or orange flavor. While not wishing to be bound by any particular theory, it is believed that when incorporating the shearform products of the present invention into other flavor bearing comestibles all flavors become simultaneously fused into one intense, long-lasting organoleptic perception.

Other flavor containing foodstuffs to which the shearform products obtained by the method of this invention can be added to provide additional flavor enhancement include ketchup, condiments, drink mixes, cake mixes, frostings and other confections such as fruit chewy, gums jellies and hard candy.

EXAMPLES

The following examples serve to provide further appreciation of the invention but are not meant in any way to restrict the effective scope of the invention. Unless indicated otherwise, the examples were carried out in a three inch diameter cable heater flash-flow apparatus of the type described in U.S. application Ser. No. 954,257 filed Sep. 30, 1992, the disclosure of which is incorporated herein by reference.

EXAMPLE 1 (COMPARATIVE EXAMPLE)

Samples of feedstock, e.g., two maltodextrins identified as "Maltrin" M365 (D.E.=36) and "Maltrin" M255 (D.E.=25), made by Grain Processing Corporation; Muscatine, Iowa, were prepared by reducing agglomerations of the maltodextrins to a free-flowing solid powder. Each material was introduced to a melt spinning apparatus having an open circular spinning head with a diameter of about 5.5 inches traveling at a rotational velocity of from about 3400 to about 3600 r.p.m. and melt spun at low temperature to provide white flakes.

Under these conditions the material was flung instantaneously against the inside surface of the spinning head which has been provided with a heat "ribbon." The heat ribbon was maintained at a relatively low temperature of from about 130° C. to about 180° C. for flash heating the maltodextrin feedstock. Unlike previous attempts to melt spin maltodextrins at "cotton candy" spinning conditions, a solid white matrix material was produced which possessed a physical and chemical structure different from the feedstock. Table 1 set forth below reports the conditions at which sugar or maltodextrin carrier undergo flash flow.

TABLE 1

| FEEDSTOCK | TEMPERATURE OF RIBBON | RPM* | PRODUCT |
| --- | --- | --- | --- |
| Sugar | 200° C. | 3600 | Fibers |
| Sugar with reducing sugar (lactose) | 210° C. | 3600 | Fibers |
| Reducing Sugar (lactose) | 224–229° C. | 3600 | Floss |
| Maltodextrin (D.E. 20) | 200° C. | 3600 | Charred Matrix unusable |
| Maltodextrin (D.E. 34–38) | 165° C. | 3600 | White chip or flake |
| Maltodextrin (D.E. 25) | 140° C. | 3600 | White chip or flake |

*Size of spinning head is 5.5 inches; head openings are slits which are 3–5 mm long by 0.5–0.75 mm wide.

From this example it can be seen that carriers such as sucrose and maltodextrin require fairly high temperatures from 140° C. to 229° C. to undergo flash-flow conditions.

EXAMPLE 2

This example shows that the use of fructose as a processing aid. Thus, when fructose was added to a maltodextrin containing feedstock used in the preparation of a dry ice cream formulation flash-flow conditions were attained at significantly reduced temperatures.

| Ingredients | Weight, Grams | Quantity, Percent |
| --- | --- | --- |
| 1. Crystalline Fructose (Staley Crystal) | 720.00 | 24.00 |
| 2. Maltodextrin (Corn Syrup Solids-Hubinger 42 DE) | 1291.50 | 43.05 |
| 3. Non-Fat Milk Solids (Mulligan) | 900.00 | 30.00 |
| 4. Best Mix Stabilizer (Germantown Mfg.) | 13.50 | 0.45 |
| 5. Medium Chain Triglyceride Oil (Stephen) | 60.00 | 2.00 |
| 6. Carboxymethylcellulose (Aqualon) | 3.00 | 0.10 |
| 7. Guar Gum Supercol UNLF (Aqualon) | 3.00 | 0.10 |
| 8. Vanilla Flavor 18042 (FF & S) | 6.00 | 0.20 |
| 9. Cream Flavor 29398 (FF & S) | 3.00 | 0.10 |
| | | 100.00% |

All ingredients except fructose, maltodextrin and non-fat milk solids were blended in a CUSINART® mixer. The fructose was pre-ground and then added together with maltodextrin and non-fat milk solids to the blend and thoroughly mixed. The blend was then spun in a flash heat process at 3600 r.p.m. and a temperature range from about 100°–115° C. Fine granules were obtained. Upon addition of tabletting lubricant the granules were directly pressed into tablets. The tablets melted in the mouth quickly and had a long-lasting intense creamy flavor.

Additionally, 50 grams of the granular product was mixed with 150 grams–200 grams of aqueous medium to obtain a liquid mixture which upon freezing resulted in a creamy tasting soft serve ice cream.

This example shows that by adding fructose at a concentration of 24% by weight to a maltodextrin-containing feedstock the amount of added heat required to enable the maltodextrin to undergo flash-flow conditions was significantly reduced. In Example 1, a feedstock made entirely of maltodextrin required 140°–165° C. to undergo flash-flow conditions. By contrast, after adding fructose, the maltodextrin-containing feedstock could be processed at temperatures from 100° to 115° C. which are significantly lower. Because flash-flow conditions are achieved at much lower temperatures, the feedstock can include fairly substantial amounts of heat sensitive materials. In this example, 30% by weight non-fat milk solids, which are well-known heat sensitive ingredients, were spun without degradation or charring. In addition, the presence of fructose in the feedstock caused the formation of a granular shearform product which was used directly for tabletting.

EXAMPLE 3

This is another example in which fructose was used as a processing aid. Fructose was added to a maltodextrin-containing feedstock. The result was a significant decrease in the amount of heat required to create flash-flow conditions in the maltodextrin portion of the feedstock. In this example, the final blend was subjected to flash-flow conditions at 3600 r.p.m. and at 122° C.

| Ingredients | Weight, Grams | Quantity, Percent |
| --- | --- | --- |
| 1. Crystalline Fructose (Staley Crystal) | 720.00 | 24.00 |
| 2. Maltodextrin (Corn Syrup Solids-Hubinger 42 DE) | 630.00 | 21.00 |
| 3. Corn Syrup Solids (Hubinger 36 DE) | 450.00 | 15.00 |
| 4. Maltodextrin (Maltrin-180) | 300.00 | 10.00 |
| 5. Non-Fat Milk Solids (Mulligan) | 840.00 | 28.00 |
| 6. Medium Chain Triglycerides Oil (Neobee M-5) | 30.00 | 1.00 |
| 7. Best Mix Stabilizer (Germantown Mfg.) | 13.50 | 0.45 |
| 8. Carboxymethylcellulose (Aqualon 7LF) | 6.00 | 0.20 |
| 7. Guar Gum Supercol (Aqualon UNLF) | 4.50 | 0.15 |
| 8. Vanilla Flavor (FFS Powder 18042) | 3.00 | 0.10 |
| 9. Cream Flavor (FFS 29398) | 3.00 | 0.10 |
| | | 100.00% |

Pre-ground fructose, maltodextrin and non-fat milk solids were thoroughly mixed. The remaining ingredients were also thoroughly mixed, added to the blend and then were mixed in thoroughly. The final blend was subjected to flash-flow conditions as explained above to obtain fine granules of dry ice cream.

Fifty grams of the granular product was mixed with 150–200 grams of aqueous medium to obtain a liquid mixture which upon freezing became a very tasty, nicely textured frozen soft ice cream.

Upon addition of lubricant, the granular product was directly pressed into very pleasant, creamy tasting tablets. The flavor was unusually long lasting.

Just as in Example 2 above, in this example, the addition of fructose allowed the maltodextrin carrier to undergo flash-flow at considerably reduced temperatures of 122° C. As a result, a high concentration of heat sensitive products such as non-fat milk solids could be included in the feedstock. A dry ice cream mix was obtained which was creamy and quite flavorful. Moreover, the addition of fructose also facilitated the formation of a granular shearform product which was directly used in tabletting. The resulting tablets had an intense creamy, long lasting flavor.

EXAMPLE 4

In this example, fructose is used to lower the temperature at which a maltodextrin bearing feedstock undergoes flash-flow conditions. Moreover, the addition of fructose to the maltodextrin carrying feedstock also facilitated tabletting. The resulting shearform product was granular and was used directly in tabletting. The ingredients used in the feedstock are shown below:

| Ingredients | Weight, Grams | Quantity, Percent |
| --- | --- | --- |
| 1. Crystalline Fructose (Staley Crystal) | 120.00 | 30.00 |
| 2. Maltodextrin Corn Syrup Solids-Dry Sweet DE42) | 92.00 | 23.00 |

-continued

| Ingredients | Weight, Grams | Quantity, Percent |
| --- | --- | --- |
| 3. Powered Sugar (6X Domino) | 168.00 | 42.00 |
| 4. Medium Chain Triglyceride Oil (Neobee M-5) | 8.00 | 2.00 |
| 5. Citric Acid (ADM anhydrous powder) | 12.00 | 3.00 |
| | | 100.00% |

Medium Chain Triglyceride (MCT) Oil was mixed with powdered sugar. The remaining ingredients were then added to the blend and were thoroughly mixed. The final blend was subjected to flash heat conditions at 119° C. and 3600 RPM. Very flavorful fine granules were obtained which upon addition of tabletting lubricant were directly compressed into tablets. Although the feedstock also contained powdered sugar as a sweetener, the temperature required to achieve flash-flow conditions in the maltodextrin carrier was not impacted.

EXAMPLE 5

In this example, fructose was used again as a processing aid which when added to a maltodextrin carrying feedstock lowered the flash heat processing temperature to 125° C. The addition of fructose also caused the final shear form product to be granular and thus useful directly in tabletting. The feedstock used in this example had the ingredients listed below.

| Ingredients | Weight, Grams | Quantity, Percent |
| --- | --- | --- |
| 1. Crystalline Fructose (Staley Crystal) | 150.00 | 30.00 |
| 2. Maltodextrin Corn Syrup Solids-Dry Sweet DE42) | 115.00 | 23.00 |
| 3. Sugar Powder (6X Domino) | 225.00 | 45.00 |
| 4. Medium Chain Triglyceride (MCT) Oil (Neobee M-5) | 10.00 | 2.00 |
| | | 100.00% |

MCT oil was thoroughly mixed with the sugar powder. The remaining ingredients were added to the blend which was thoroughly mixed. The blend was subjected to flash heat conditions at 3600 RPM and 125° C., a considerably lower temperature than the flash heat temperature of maltodextrin. Fine granules of shearform product were obtained which upon addition of lubricant could be used directly in tabletting. The shearform product obtained in this example could be used together with other confectionery ingredients to form excellent confectionery tablets. The shearform product obtained in this example could also be used as excipient for other actives such as medicament, food acids, flavors, spices and salt.

EXAMPLE 6

In this example fructose was used not only as a processing aid, but also as flavor enhancer. The ingredients are set forth below.

| Ingredients | Weight, Grams | Quantity, Percent |
| --- | --- | --- |
| 1. Granular Shearform Product of Example 4 | 195.10 | 97.55 |
| 2. Magnesium Stearate (Whittaker) | 3.00 | 1.50 |
| 3. Cherry Flavoring | 0.80 | 0.80 |
| 4. Color, Red (FDC #40) | 0.10 | 0.20 |
| 5. SYLOID ® 244 (Please provide manufacturer) | 0.25 | .50 |
| | | 100.00% |

The granular shearform product obtained in Example 4 above was mixed with small amounts of tabletting lubricant such as magnesium stearate and SYLOID® and trace amounts of cherry flavoring and red color. The resulting mixture was directly compressible into confectionery tablets. The tablets had an intense, long lasting cherry flavor and melted easily in the oral cavity.

Thus, in the granular shearform product obtained in Example 4 fructose was used as a processing aid. In forming the intensely cherry flavored tablets, fructose was used as a flavor enhancer.

EXAMPLE 7

In this example, fructose was used both as a processing aid and a flavor enhancer to obtain intensely orange flavored confectionery tablets. The feedstock included the ingredients set forth below.

| Ingredients | Weight, Grams | Quantity, Percent |
| --- | --- | --- |
| 1. Granular Shearform Product of Example 4 | 194.80 | 97.45 |
| 2. Magnesium Stearate (Whittaker) | 3.00 | 1.50 |
| 3. Flavoring: Orange 23367 (Please specify manufacturer) | 1.60 | 0.80 |
| 4. Color, Orange (FDC #10, Lake) | 0.25 | 0.50 |
| 5. SYLOID ® 244 | 0.25 | .50 |
| | | 100.00% |

The shearform product obtained in Example 4 above was mixed with small amounts of tabletting lubricant and trace amounts of orange flavoring and color. The resulting mixture was directly compressible into confectionery tablets. The tablets had an intense, immediate and long lasting orange flavor where the fructose and orange flavor were fused into one excellent orange flavor.

Thus, while there have been described what are presently believed to be the preferred embodiments of the present invention, those skilled in the art will appreciate that other and further modifications can be made without departing from the true scope of the invention, and it is intended to include all such modifications and changes as come within the scope of the claims as appended herein.

What is claimed:

1. In a method for converting feedstock, which contains a heat sensitive ingredient and a carrier selected from a maltodextrin and polydextrose, to a shearform product by subjecting the feedstock to flash flow processing, the improvement comprising:

adding fructose to said feedstock in at least an amount sufficient to reduce the amount of added heat required to create flash flow conditions in the carrier portion of said feedstock during said flash flow procesing.

2. The improved method of claim 1, wherein the reduced amount of heat is that required to induce flash flow at a temperature less than 10°–25° C. degrees below the flash flow temperature of said feedstock without said fructose.

3. The improved method of claim 1, wherein said feedstock comprises a component selected from the group consisting of frozen food ingredients, confectionery ingredients, dry beverage ingredients, cake mix ingredients and flavorants.

4. The improved method of claim 1, wherein said feedstock contains a non-fructose carrier having at least 30% thereof selected from the group consisting of maltodextrin, polydextrose, and mixtures thereof.

5. A method of improving a comestible shearform product made from a feedstock which includes a heat sensitive ingredient and a carrier selected from a maltodextrin and polydextrose, said method comprising:

modifying said feedstock by addition of fructose in at least an amount sufficient to reduce the amount of added heat required to create flash flow conditions in the carrier portion of said feedstock and subjecting said feedstock to flash flow processing.

6. The method of claim 5, wherein said amount of added fructose is sufficient to provide flavor enhancement.

7. The method of claim 5, wherein said amount of a fructose is from about 5% to about 50% by weight of said feedstock.

8. The method of claim 7, wherein said amount of a fructose is from about 10% to about 40% by weight of said feedstock.

9. The method of claim 5, wherein said feedstock contains a non-fructose carrier having at least 30% thereof selected from the group consisting of maltodextrin, polydextrose, and mixtures thereof.

10. The method of claim 5, wherein said feedstock comprises a component selected from the group consisting of frozen food ingredients, flavorants, food acids, confectionery ingredients, dry beverage ingredients, cake mix ingredients and condiments.

11. The method of claim 10, wherein said flavorants are sweeteners selected from the group consisting of natural and artificial sweeteners and mixtures thereof.

12. The method of claim 11, wherein said sweeteners are artificial sweeteners selected from the group consisting of saccharine, saccharine salts, cyclamic acid, cyclamic acid salts, aspartame, sucralose, acesulfame and combinations thereof.

13. The method of claim 11, wherein said sweeteners are natural sweeteners selected from the group consisting of sucrose, maltose, dextrose, ribose, lactose, glucose, arabinose, mannose, pentose, sorbose, xylose, galactose, sorbitol, mannitol, galactitol, lactitol, maltitol, and mixtures thereof.

14. The method of claim 10, wherein said food acids are selected from the group consisting of malic acid, citric acid, tartaric acid, adipic acid, fumaric acid, ascorbic acid and mixtures thereof.

15. The method of claim 10, wherein said frozen food ingredients include hydrogels, emulsifiers, nutritional supplements, dehydrated vegetable fluids, nonfat milk solids, dehydrated animal fluids, vitamins and minerals.

16. A comestible comprising:

an enhanced shearform product prepared by subjecting to flash flow processing a feedstock which contains a heat sensitve ingredient and a carrier selected from one of a maltodextrin and polydextrose, and which is modified by addition of fructose in at least an amount sufficient to reduce the amount of added heat required to create flash flow conditions in the carrier portion of said feedstock during said flash flow processing.

17. The comestible of claim 16, wherein said amount is increased to provide additional flavor enhancement.

18. The comestible of claim 16, wherein said amount of fructose is from about 5% to about 50% by weight of said feedstock.

19. The comestible of claim 18, wherein said amount of fructose is from about 10% to about 40% by weight of said feedstock.

20. The comestible of claim 16, wherein said feedstock contains a non-fructose carrier having at least 30% thereof selected from the group consisting of maltodextrin, polydextrose, and mixtures thereof.

21. The comestible of claim 16, wherein said feedstock comprises a component selected from the group consisting of frozen food ingredients, confections, food acids, dry beverage ingredients, cake mix ingredients, condiments and flavorants.

22. The comestible of claim 16, wherein said enhanced shearform product is a granular matrix which is compressed to form a tablet.

23. The comestible of claim 15 which is a confectionery tabletting ingredient.

24. The comestible of claim 15 which is a dry beverage ingredient.

25. The comestible of claim 15 which is cake mix ingredient.

* * * * *